(12) United States Patent
Tessarin (10) Patent No.: US 10,773,070 B2
(45) Date of Patent: Sep. 15, 2020

(54) FLUID FLOW SWITCHING DEVICE FOR CATHETERIZATION WITH A THREE WAY BLADDER CATHETER

(71) Applicant: Andrea Chiapatti, Monteveglio di Valsamoggia (IT)

(72) Inventor: Alessandro Tessarin, Ferrara (IT)

(73) Assignee: Andrea Chiapatti, Monteveglio di (IT)

( * ) Notice: Subject to any disclaimer, the term of this patent is extended or adjusted under 35 U.S.C. 154(b) by 411 days.

(21) Appl. No.: 15/575,745

(22) PCT Filed: May 24, 2016

(86) PCT No.: PCT/IB2016/053035
§ 371 (c)(1),
(2) Date: Nov. 20, 2017

(87) PCT Pub. No.: WO2016/189462
PCT Pub. Date: Dec. 1, 2016

(65) Prior Publication Data
US 2018/0117298 A1    May 3, 2018

(30) Foreign Application Priority Data

May 25, 2015   (EP) ..................................... 15169074

(51) Int. Cl.
*A61M 39/22*       (2006.01)
*A61M 25/00*       (2006.01)

(52) U.S. Cl.
CPC ...... *A61M 39/223* (2013.01); *A61M 25/0017* (2013.01); *A61M 25/0029* (2013.01); *A61M 2210/1085* (2013.01)

(58) Field of Classification Search
CPC .......... F16K 11/00; F16K 11/02; F16K 11/06; F16K 11/072; F16K 11/076;
(Continued)

(56) References Cited

U.S. PATENT DOCUMENTS 4,704,102 A    11/1987   Guthery
6,096,013 A     8/2000   Hakky et al.
(Continued)

FOREIGN PATENT DOCUMENTS

| DE | 632579 C | 9/1936 |
|---|---|---|
| WO | WO 2007/116386 A1 | 10/2007 |
| WO | WO 2008/089985 A1 | 7/2008 |

*Primary Examiner* — Tiffany Legette
(74) *Attorney, Agent, or Firm* — R. Neil Sudol; Henry D. Coleman (57) ABSTRACT

A flow switching device for catheterization via a three way catheter has a housing with four openings, and first, second and third distal hydraulic conduits originating at the first, second and third openings, respectively. A switch enables changes among a first operative configuration wherein the first and third openings are in communication, a second operative configuration wherein the second and fourth openings are in communication, and a third operative configuration wherein the first and second openings are in communication, and a fourth operative configuration wherein the second and third openings are in communication. A hydraulic bifurcation with a respective proximal hydraulic branch originates from the fourth opening, and fourth and fifth distal hydraulic conduits originating distally from the proximal hydraulic branch are in fluid dynamical communication with each other.

19 Claims, 4 Drawing Sheets

(58) Field of Classification Search
CPC ... F16K 11/085; A61M 39/223; A61M 39/22; A61M 39/162; A61M 39/16; A61M 25/0029; A61M 2210/1085; A61M 39/233; A61M 25/0017
See application file for complete search history.

(56) References Cited

U.S. PATENT DOCUMENTS

2010/0305507 A1* 12/2010 Duncan ............. A61M 5/14526
604/121
2014/0364833 A1* 12/2014 Christensen ........ A61M 39/223
604/507

* cited by examiner

FLUID FLOW SWITCHING DEVICE FOR CATHETERIZATION WITH A THREE WAY BLADDER CATHETER

TECHNICAL FIELD

The present invention relates to the field of medical devices usable in health care procedures in which it is needed to manage the flow of a fluid, preferably a liquid, in the body of a patient, in particular in urology, more specifically when it is needed the usage of a three way bladder catheter.

BACKGROUND ART

The three way bladder catheter is used in the post-operative treatment of bladder or prostate surgery to drain bladder and/or prostate bleedings, respectively. It is provided with a triple lumen branching in three distinct ways at a first end. A second end of the catheter is provided with an inflatable balloon, which represents the end of the second way, while the first and the third ways are open at both the ends of the catheter. The second end of the catheter is introduced and anchored in the urethra up to the bladder and anchored thereto conveying the saline solution in the balloon through the second way of the catheter. The continuous urine and blood flow out of the body of the patient from the bladder occurs through the first way of the catheter which, to such aim, is connected to an urine collection device, typically an urine collection bag.

To carry out a bladder "automatic" continuous washing, called "cystoclysis", a washing liquid coming from a respective supplying system is conveyed thereto through the third way of the catheter to which such system is connected.

To guarantee the complete drainage of the coagula present in the bladder, to des-obstruct the bladder catheter and to avoid the occlusion of the respective first way, it is also needed to carry out periodically another procedure, called "cystolusis". This last one provides a plurality of consecutive washings of the bladder, typically carried out manually by the operator. To carry out the cystolusis, the operator has to wear: mask, disposable gloves, white coat and safety glasses. In addition it is to arrange a sterile disposable cloth between the legs of the patient; to position a sterile basin thereon; to disconnect the urine collection device connected to the first way; to lean the first end of the catheter on the basin; to throw away the urine collection device; to throw away the disposable gloves; to wash ones hands; to wear sterile gloves; to hold the catheter with the not dominating hand and to practice the des-obstructing washing with the dominant hand by carrying out the following operations cyclically: to suck the saline from the bottle by means of a cone syringe/sterile catheter; to join the syringe to the first way of the catheter; to inject the saline at low pressure in said first way through the syringe; to suck, by means of the syringe, the drainage liquid and coagula; to disconnect the syringe from the catheter and to throw the discarded aspirate in the basin up to the complete drainage of the coagula and/or des-obstruction of the catheter. After that it is needed to throw away the dirty gloves and to wear new clean ones; to connect a new urine collection bag to the first way of the catheter; to throw all the disposable material used in the special waste container; to disinfect and to sterilize the basin; and finally, to remove the individual protection devices or "IPD" used and to throw them away in the suitable special waste container, if contaminated, or in the urban waste, if not contaminated.

Therefore, the cystolusis, when carried out as above described, implies the interruption of the sterile hydraulic circuit system used for the cystoclysis with consequent risk of urinary tract infections onset (called "UTI"). These last ones imply the interruption of the healing process of the patient with worsening of the clinical picture, lengthening of hospitalization times and use, when possible of suitable antibiotics chosen on the basis of the type of bacteria causing the infection. Such antibiotics can be also particularly expensive. Moreover, some types of bacteria cannot be eradicated (for example *Klebsiella Pneumonie*).

In addition, the interruption of the sterile circuit implies a high biological risk for the operator. In fact, he can be contaminated by coming in contact to urine, washing liquid and blood.

Moreover, it is to be considered that to guarantee a good patency of the bladder catheter, the "cystolusis" is carried out normally at least three times a day, and in case of macrohaematuria or of obstructions of the first way, generally it is regularly repeated more than three times. Therefore, high costs result connected to the cystolusis per se, due to the performance costs, the materials and the disposable IDP and the disposal of the corresponding waste, and above all, to the UTI related thereto. In case of severe haematuria, also the third way of the catheter can be obstructed. Therefore, the steps above described in relation to the des-obstruction of the first way of the catheter have to be repeated by joining the syringe to the third way of the catheter instead to the cited first way. Obviously, this implies that the procedure relative to the cystolusis becomes longer with consequent increase in biological risks for the operator and discomfort of the patient.

DISCLOSURE OF INVENTION

Aim of the present invention is to overcome the above described drawbacks of the state of the art and in particular to reduce UTI; to reduce costs relative to cyctolusis per se as well as to the pathologies related thereto.

Another aim of the invention is to render the cystolusis more tolerable for the patient and easier for the operator to carry out, in particular reducing performance times and costs and the biological risk related thereto.

Another aim of the invention is to provide means for carrying out both cystoclysis and cystolusis, which are structurally easy and economic as well as reliable in use and which avoid the opening of the closed circuit between the catheter and the supplying system and the urine collection device, namely of the sterile hydraulic circuit system used for the cystoclysis.

Such aims can be attained by means of a fluid flow switching device for catheterization, with a three way bladder catheter, according to the independent claim.

As it will be clear in the following, said switching device can be suitably connected hydraulically and at the same time: to the first way of a three way catheter introduced in a bladder; to the third way of said catheter; to an urine collection device; to a washing liquid supplying system; and to a liquid suction and pumping device, which hereinafter will be referred as liquid suction device for concision aim. As hereinafter it will be explained in detail, thus connected, in this hydraulic arrangement, the switching device, in the first operative configuration, can be used to carry out cystoclysis. Moreover, in the respective second, third and fourth operative configurations, the device can be used to carry out the various operative steps of the cystolusis without disconnecting the three way catheter from the urine collection device; nor from the washing liquid supplying system. Therefore, said closed circuit is not interrupted. As a consequence, the onset of UTI is drastically reduced. In addition, the cystolusis does not imply a high biological risk for the operator carrying out it and the respective costs are reduced since the above cited materials and disposable IPD are no longer needed. Moreover, it is to be noted that, always without interrupting the closed circuit, it is possible to des-obstruct also the third way of said catheter.

As it will be evident hereinafter, according to the invention, the same hydraulic circuit system can be used for performing both cystoclysis and the cystolusis operating optional interrupting flow devices, which can be present downstream of the first, second and third distal hydraulic conduit 1, 2, 3 and proximal hydraulic branch 6, such that to connect, each other, only the two of them communicating with the opening indicated in each of the operative configurations.

It is to be considered that the switching device according to the invention, in each configuration, can allow only the connection of two between the first, second and third distal hydraulic conduit 1, 2, 3 and proximal hydraulic branch 6. It is avoided that the operator connects accidentally, each other, more than two between the first, second and third distal hydraulic conduit 1, 2, 3 and proximal hydraulic branch 6, as. This guarantees correct cystoclysis and cystolusis procedures.

Moreover, it is very important that each element of the switching device according to the invention, in particular the switching means, are realized easily and economically. Finally, the disclosed switching device can be advantageously used also in other therapeutic fields, such for example chemotherapeutic treatments to prevent recurrence of a superficial bladder cancer. These last ones provide intravesical instillations of chemotherapeutics through a three way catheter.

BRIEF DESCRIPTION OF THE DRAWINGS

In the present description and in the claims, the terms "connection" and the verb "to connect" mean fluid, in particular hydraulic connections, and when not indicated with the term "catheter" or "three way catheter" it is intended a three way bladder catheter. Moreover, the terms "operative configuration" means a configuration usable to carry out a cystolusis or cystoclysis step.

The features of the invention will be highlighted in the following, in which relative preferred embodiments will be described with reference to the appended drawings, in which.

BEST MODE FOR CARRYING OUT THE INVENTION

In FIGS. 3-6, for clarity, the sectioned surfaces are not indicated with the conventional dash line.

Referring to FIGS. 1-6, a fluid flow switching device for catheterization with a three way bladder catheter (not shown) is indicated with 100. In such figures, the realizable fluid flows are indicated in dash line and the respective arrows indicate the direction thereof. Said fluid flow switching device 100 for catheterization with a three way bladder catheter comprises:

a housing 7;

a first, second, third and fourth opening 11, 12, 13, 14 obtained in the housing 7;

a first, second and third distal hydraulic conduit 1, 2, 3, originating at the first, second and third opening 11, 12, 13, respectively;

switching means 20 designed for engaging with the housing such that in a first operative configuration make communicating the first opening 11 with the third opening 13; in a second operative configuration make communicating the second opening 12 with the fourth opening 14; in a third operative configuration make communicating the first opening 11 with the second opening 12; in a fourth operative configuration make communicating the second opening 12 with the third opening 13; and hydraulic bifurcation 17 comprising: a respective proximal hydraulic branch 6 originating from said fourth opening 14, a fourth and fifth distal hydraulic conduit 4, 5 originating distally from said proximal hydraulic branch 6 and which are fluid dynamically communicating with respect to each other.

Preferably, in the first operative configuration, the switching means 20 make communicating only the first opening 11 with the third opening 13.

Advantageously, in the second operative configuration, the switching means 20 make communicating only the second opening 12 with the fourth opening 14.

Preferably in the third operative configuration, the switching means 20 make communicating only the first opening 11 with the second opening 12.

It is preferable that, in a fourth operative configuration, the switching means 20 make communicating only the second opening 12 with the third opening 13.

Analogously, it is preferable that, in each operative configuration, the switching means 20 make communicating the relating above-mentioned openings only, since in each operative configuration the switching device allows to connect only two between the first, second and third distal hydraulic conduit 1, 2, 3 and proximal hydraulic branch 6. It is avoided that, accidentally, the operator can connect more of two between the first, second and third distal hydraulic conduit 1, 2, 3 and proximal hydraulic branch 6. This assure correct and simplified cystoclysis and cystolusis procedures. Indeed, the operator has not to take an action on the interrupting flow devices, which can be present downstream of the first three distal hydraulic conduits 1, 2, 3 and proximal hydraulic branch 6. Moreover, this renders superfluous the presence of said the interrupting flow devices, since the switching means execute the same function of the interrupting flow devices.

According to an aspect particularly preferred of the invention, the switching means 20 are at least partially introducible in the housing 7. The five distal conduits 1, 2, 3, 4, 5 of the switching device 100 according to the invention can be connected hydraulically at the same time in the following hydraulic arrangement, in which:

the first distal conduit 1 is connected to the first way of a three way bladder catheter, which, we remember, is arranged for the urine flow from the bladder;

the second distal conduit 2 is connected to a liquid suction device (typically a truncated/conical syringe), not shown;

the third distal conduit 3 is connected to a drainage tube of an urine collection device, not shown;

a fourth distal conduit 4 is connected to the third way of said three way bladder catheter, which is arranged to convey a washing liquid in bladder; and the fifth distal conduit 5 is connected to an infusion tubing of a sterile washing liquid supplying system.

According to an aspect particularly preferred of the invention, in each embodiments disclosed and fitting in the scope of the claims, the fourth and the fifth distal conduits 4, 5 can be always connected fluid dynamically. Therefore, with said hydraulic arrangement and in any operative configuration of the switching device 100, washing liquid is conveyed continuously from the respective supplying system to the bladder through: the fifth conduit 5; the fourth conduit 4; and the third way of the catheter. This allows advantageously maintaining irrigated the bladder without interruptions both during the cystoclysis and during the cystolusis, and during the passage from the one procedure to the other one. In such way, a constant cleaning of the bladder is guaranteed.

According to a further embodiment, the first, second and third distal hydraulic conduit 1, 2, 3 and the hydraulic bifurcation 17 are external to the housing 7, the switching means 20 are at least introducible in the housing 7 and comprising a greater hydraulic pipeline 15 and a smaller hydraulic pipeline 16, wherein all said openings 11, 12, 13, 14, greater hydraulic pipeline 15 and smaller hydraulic pipeline 16 are configured and arranged so that with the switching means 20 at least partially introduced in the housing 7 and, after mutual rotations of the switching means 20 with respect to the housing 7, the switching device can assume:

the first and the second operative configuration, in each one of which, the greater hydraulic pipeline 15 connects only two not consecutive openings 11, 12, 13, 14 and in which the smaller hydraulic pipeline 16 does not connect any opening 11, 12, 13, 14; and the third and fourth operative configuration, in each one of which, the smaller hydraulic pipeline 16 connects only two consecutive openings 11, 12, 13, 14 and in which the greater hydraulic pipeline 15 does not connect any opening 11, 12, 13, 14.

This consents to realize the switching means in a simple and economic way, for example starting from a full cylinder (for example in plastic material), of suitable diameter, obtaining innerly the greater and smaller hydraulic pipelines 15, 16 by means of a drill or other suitable tool.

Preferably, the greater hydraulic pipeline 15 has a length which is greater than a length of smaller hydraulic pipeline 16.

According to a preferred embodiment:

the housing 7 is cylindrical and delimited internally and laterally by a first cylindrical surface 9 which is lateral and internal, the housing 7 being accessible in parallel to the first cylindrical surface 9;

the first, second, third and fourth opening 11, 12, 13, 14 are arranged substantially along a circumference of the first cylindrical surface 9, the one after the other one, angularly spaced of a first angle β between 80° and 100°;

the switching means 20 comprise a second cylindrical surface 29 which is lateral, outer, holed and introducible in said housing 7 in parallel to the first cylindrical surface 9; and which has such a diameter that, when it is introduced in the housing 7, it is adjacent in strict adherence to said first cylindrical surface 9 to allow to be held in said housing 7 and to close at least two of said openings 11, 12, 13, 14, at respective not holed portions and after mutual rotations with respect to the first cylindrical surface 9;

the greater hydraulic pipeline 15 is internal and which connects a first and a second through hole 21, 22, obtained in the second cylindrical surface 29 and angularly spaced with respect to each other of a second angle ψ between 170° and 190°;

the smaller hydraulic pipeline 16 is internal; arranged laterally to the greater hydraulic pipeline 15 and connects a third and fourth through hole 23, 24, obtained in the second cylindrical surface 29 laterally and substantially coplanarly to said first and second through holes 21, 22, wherein all said openings 11, 12, 13, 14 and all said through holes 21, 22, 23, 24 are configured and arranged so that with the second cylindrical surface 29 introduced in the housing 7 and, after mutual rotations of the second cylindrical surface 29 with respect to the first cylindrical surface 9, the switching device 100 can assume said first, second third and fourth operative configurations.

This consents the assembling of the device according to the invention providing the introduction by pressure of the second tubular surface in the housing guarantying an effective hydraulic sealing of the switching device. In said hydraulic arrangement and in the first operative configuration (FIGS. 1 and 3), while the washing liquid is conveyed from the respective supplying system to the bladder, the switching means 20, and in particular, the relating greater hydraulic pipeline 15 (when provided) connect the first to the third distal conduit 3 and so connect the first way of the three way catheter to the urine collection device. This allows carrying out cystoclysis.

In the second operative configuration (FIG. 4), the switching means 20, and in particular the greater hydraulic pipeline 15 (when provided) connect the second distal tube to the respective proximal hydraulic branch 6, which in turn is connected to the fourth and fifth distal conduit 4, 5. Therefore, due to the high fluid dynamic resistance of the third way of said catheter, in the second operative configuration, the suction device can suck only the washing liquid from the respective supplying system. In addition, with the switching device 100 according to the invention in the operative configuration it is possible to des-obstruct also the third way of said catheter without interrupting the closed circuit. In fact, after sucking the washing liquid, it is enough to close the infusion tubing of the washing liquid supplying system and acting on the suction device, to convey the sucked liquid in bladder through the third way. Preferably, the consequent drainage liquid is then drained from the bladder to the suction device with the switching device 100 configured in the following third operative configuration.

In the third operative configuration (FIG. 5), the switching means 20, and in particular the smaller hydraulic pipeline 16 (when provided), connect the first to the second distal conduit 2 connecting the first way of the catheter to the suction device. This allows to convey in the bladder, through the first way of the catheter, the sucked washing liquid and, in the following, to convey a consequent drainage liquid from the bladder to the suction device.

In the fourth operative configuration (FIG. 6), the switching means 20, and in particular the smaller hydraulic pipeline 16 (when provided), connect the second distal conduit 2 to the third distal conduit 3 and so the suction device to the urine collection device.

It is to be noted that the dimensions of said openings 11, 12, 13, 14 and of said holes 12, 22, 23, 24 are such that it is practically impossible that the operator connects accidentally a distal hydraulic conduit 1, 2, 3, 4 to more than one remaining distal hydraulic conduits 1, 2, 3, 4. This avoids that, for example, the sucked drainage liquid can be re-conveyed in bladder through the first or second way of catheter while it is conveyed in the urine collection device.

Figure 1:
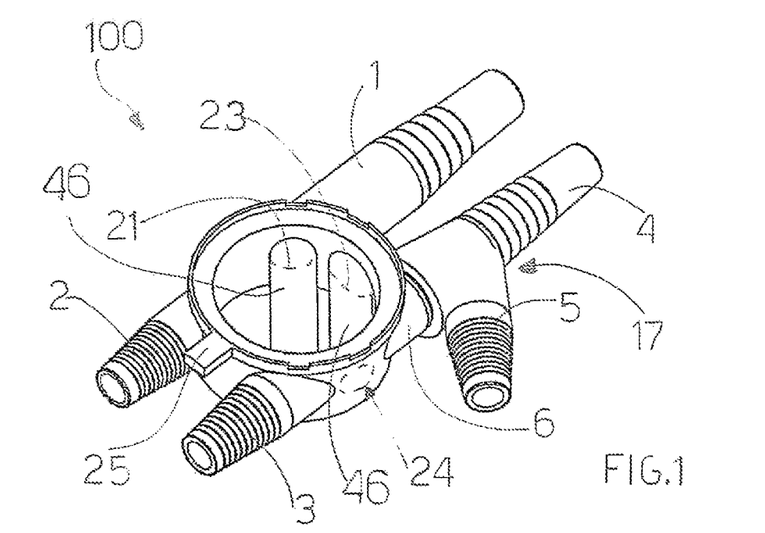
FIG. 1 is a perspective view of an embodiment of the switching device according to the invention in a first operative configuration.
Figure 2:
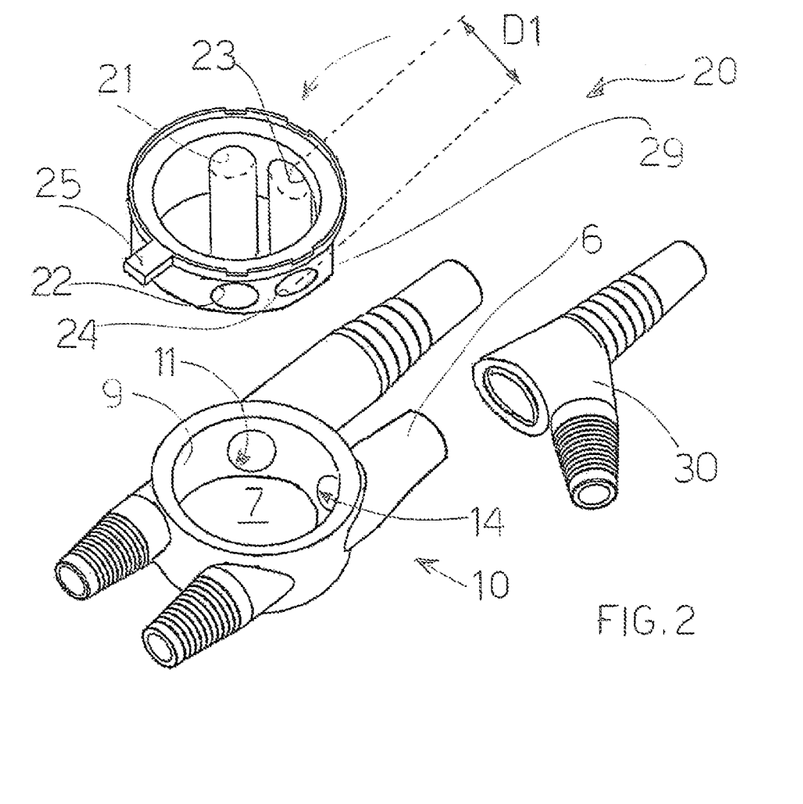
FIG. 2 is a perspective and exploded view of the device of FIG. 1.
Figure 3:
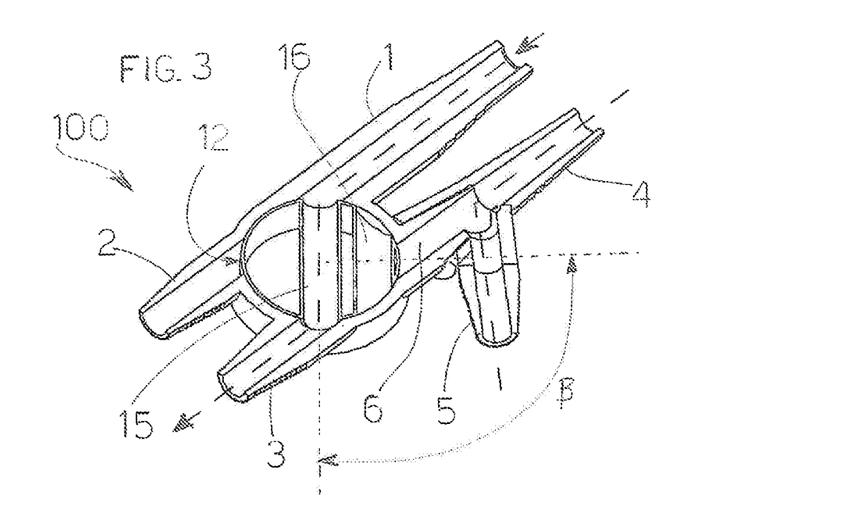
FIG. 3 is a perspective view, in longitudinal section, of the device of FIG. 1.
Figure 4:
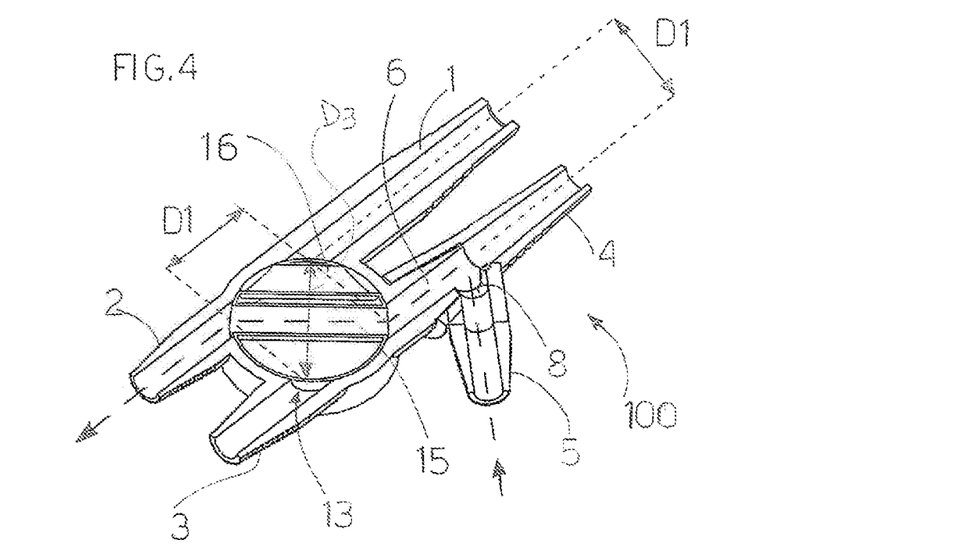
FIGS. 4-6 are perspective views and in longitudinal section, of the device of FIG. 1, in a second, third and fourth operative configuration, respectively.

Referring to FIG. 4, according to an aspect of the invention, the openings 11, 12, 13, 14 are substantially arranged at the vertexes of a square inscribable in said circumference and having a side of length D1 (see FIG. 4). Preferably, such openings 11, 12, 13, 14 are arranged the one after the other one angularly spaced of a first angle β (see FIG. 3) substantially between 85° and 95°, preferably between 88° and 92°, more preferably between 89° and 91°.

Preferably, the openings 11, 12, 13, 14 are centred with respect to said vertexes, in such case, they result angularly equidistant of a first angle β substantially equal to 90°. This simplifies the design and the realization of the switching device 100. Therefore, said first, second, third and fourth openings are arranged the one after the other one at a respective spacing D1 (centrally measured with respect to the openings 11, 12, 13, 14). Therefore, as a consequence, two not consecutive openings result substantially diametrally opposed with respect to such circumference, and arranged at a mutual second spacing (centrally measured with respect to the openings) equal to the diameter of said circumference, therefore they are substantially diametral the one with respect to the other one. In such case, it is preferable that said first and second holes are obtained substantially diametrally with respect to each other (i.e. angularly spaced of a second angle ψ substantially equal to 180°) and that said third and fourth holes are angularly spaced of a third angle substantially equal to 90°, i.e. arranged at a mutual second spacing substantially equal to said first spacing D1 (since for the present invention, it is assumed that the side of the square inscribable in said circumference is substantially equal to the one of a square inscribable in another circumference respective to the second tubular surface). Anyway, by suitably dimensioning the through holes 21, 22, 23, 24 and the openings 11, 12, 13, 14 it is possible to balance the angulation of said openings and said holes.

Preferably, the conduits 1, 2, 3, 4, 5 are directly connectable to said catheter, the drainage tube, the infusion tubing and the suction device and to this aim they can be provided with respective tapered distal ends. Also the proximal hydraulic branch 6 is advantageously provided with a respective tapered distal end.

According to a particularly preferred aspect of the invention, the switching means 20 are realized as a single body. Preferably, the switching means 20 are realized as a single body and are obtainable, or can be obtained by moulding. In such case, they are not provided with respective elements to be assembled, for example by gluing or welding. Moreover, the moulding allows a very effective mechanical calibration of the coupling with the housing 7. In addition, this allows to render the switching device 100 sealed by simply introduction by pressure of the second surface of the housing 7. Such feature is fundamental for the function for which the switching device 100 has been designed, since all the hydraulic connections are efficiently separated from the outside.

Advantageously, the switching means 20 comprise a first and a second hydraulic tube 45, 46 that define internally said greater hydraulic pipeline 15 and said smaller hydraulic pipeline 16 respectively. The first and second hydraulic tube 45, 46 are realized as a single body with the second cylindrical surface 29 to form a first structural element 20 (FIG. 1) obtainable by moulding. In such way, it is particularly simplified the realization of the switching device 100.

According to a particularly preferred aspect, said first, second and third distal hydraulic conduit 1, 2, 3 and the proximal hydraulic branch 6 are realized as a single body with said first cylindrical surface 9 to form a second structural element 10 obtainable, or obtained, by moulding. In addition, the switching device 100 comprises a three way hydraulic fitting 30 (FIG. 2) hydraulically connectable to said proximal hydraulic branch 6 to provide said hydraulic bifurcation 17 together with said proximal hydraulic branch 6. This further simplifies the realization of the switching device 100 and its respective assembly.

It is preferable that the first way of the three way hydraulic fitting 30 could be fitted on said proximal hydraulic branch 6 with the respective remaining two ways which define said fourth and fifth distal hydraulic conduit 4, 5, respectively. When, as in the appended figures, the first way fits the hydraulic branch with the connection of the three ways arranged at the proximal hydraulic branch 6, this latter can be provided with another through hole 8 to connect hydraulically the proximal hydraulic branch 6 to the fifth distal hydraulic conduit 5. Alternatively, the first way of the three-way hydraulic fitting 30 can have greater length than the proximal hydraulic branch 6, so that the connection of the three ways is arranged outside the proximal hydraulic branch 6.

According to another aspect of the invention, said first, second and third distal hydraulic conduit 1, 2, 3, the proximal hydraulic branch 6, the fourth and the fifth distal hydraulic conduit 4, 5 are realized as a single body with said first cylindrical surface 9 to form a structural element comprising said second structural element 10.

The greater hydraulic pipeline 15 and/or the smaller hydraulic pipeline 16 can be rectilinear. In addition to simplify the realization of the switching means 20, this avoids also that such hydraulic pipelines 15, 16 have areas in which the liquid can stagnate and favour the accumulation of blood coagula. Therefore, such pipelines do not need respective washing procedures before passing from an operative configuration to the other one.

Moreover, it is preferred an embodiment of the switching device 100 in which the greater hydraulic pipeline 15 and the smaller hydraulic pipeline 16 are parallel with respect to each other.

According to an aspect of the invention, said first, second, third and fourth opening 11, 12, 13, 14, said first, second, third and fourth hole 21, 22, 23, 24 have preferably the same dimensions. This allows to obtain more regular hydraulic flows and to guarantee high sealing.

It is particularly preferred that the first, second, third and fourth distal hydraulic conduit 1, 2, 3, 4 are coplanar with respect to each other to minimize the space taken by the switching device 100 thus reducing the discomfort of the patient. Moreover, in such case, said second structural element 10 and/or said structural element are easier to be produced.

Figure 5:
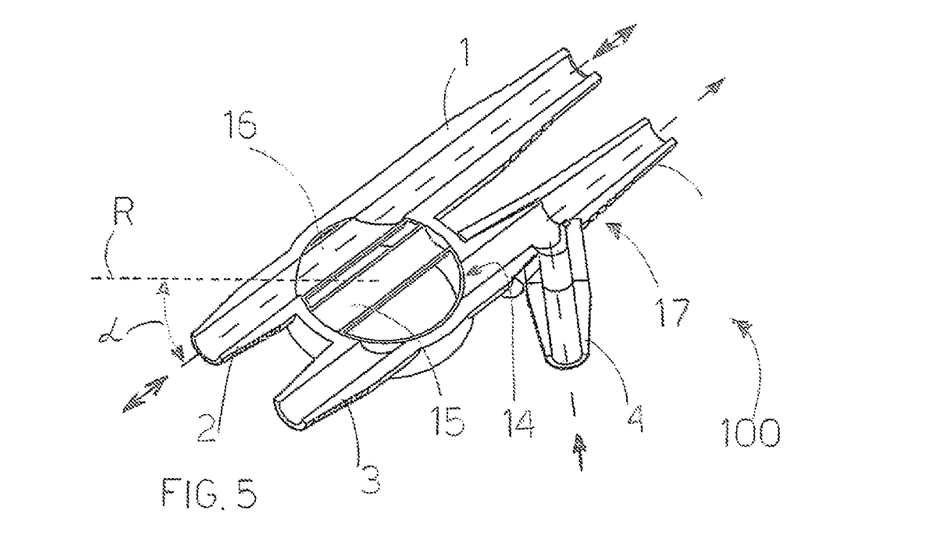
Figure 6:
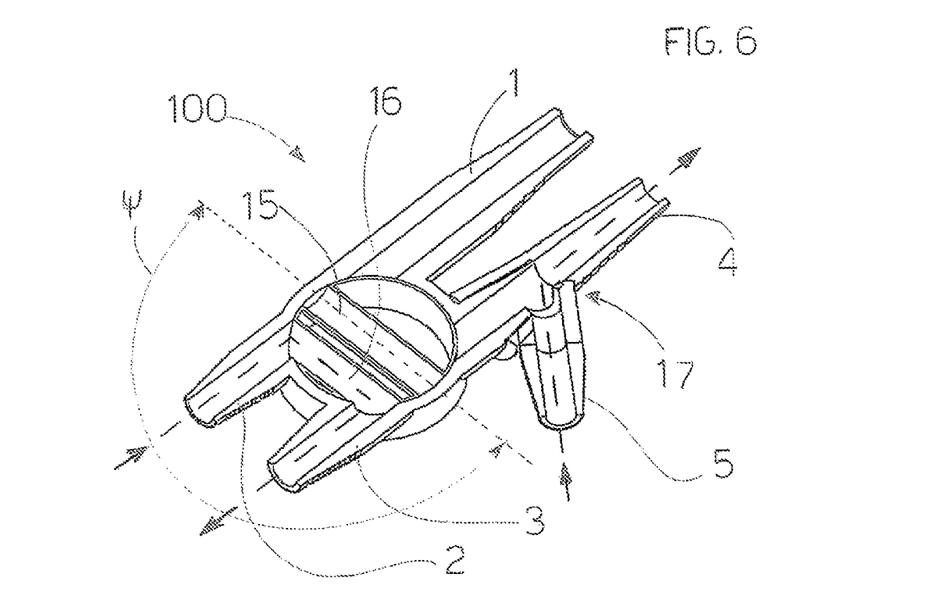

It is preferable that the first, second, third and fourth distal hydraulic conduit 1, 2, 3, 4 are substantially coplanar, rectilinear and inclined with respect to a radial direction R, passing across the centre of the circumference of the first cylindrical surface and across the centre of the respective opening of a fourth angle α between 20° and 45° (see FIG. 5). In such way, the switching device 100 is less cumbersome and this guarantees more ergonomic positioning and less discomfort for the patient. In addition, while the fourth angle α increases, the bending of the connection tubes between the distal hydraulic conduits 1, 2, 3, 4, and: the three way catheter; the urine collection device and the suction device is more avoided. On the contrary, there will be an increasing bending while the fourth angle α is reduced. Therefore, the efficacy of the switching device 100 increases while the amplitude of the fourth angle increases. For such reason, it is increasingly preferable that the fourth angle α is between 30° and 45°; 35° and 45°; 40° and 45°. Advantageously, the fourth angle α is substantially equal to 45° since as a consequence the first, second, third and fourth distal hydraulic conduit 1, 2, 3, 4 are parallel with respect to each other and available in parallel to the legs of the patient. Therefore, the switching device 100 is yet less cumbersome and so less troublesome for the patient and bending of said connection tubes is avoided.

In order that the switching device 100 is rendered yet less cumbersome and that it is avoided that the connection tube with the infusion tubing of the supplying system bends, it is preferable that the fifth distal hydraulic conduit 5 has a respective longitudinal axis forming a fifth angle between 135° and 160° (preferably equal to 160°) with the longitudinal axis of the fourth distal tube 4.

This improves the conveying of the washing liquid from respective supplying system to the third way of the catheter. In such case, when the first, second, third and fourth distal hydraulic conduit 1, 2, 3, 4 are coplanar, it is preferable that the longitudinal axis of the fifth distal hydraulic conduit 5 is arranged on a plane inclined of 45°-90° (preferably 90°) with respect to the plane in which the remaining distal hydraulic conduits 1, 2, 3, 4 lie.

Advantageously, the switching means 20 comprise a grasp element 25 (FIGS. 1 and 2) to carry out said mutual rotations. The grasp element 25 is arranged superiorly on the second cylindrical surface 29 and, preferably, outside the housing 7. Moreover, it can be realized as a single body as well with the second cylindrical surface 7, and comprised in said second structural element 20 obtainable by moulding.

Figure 7:
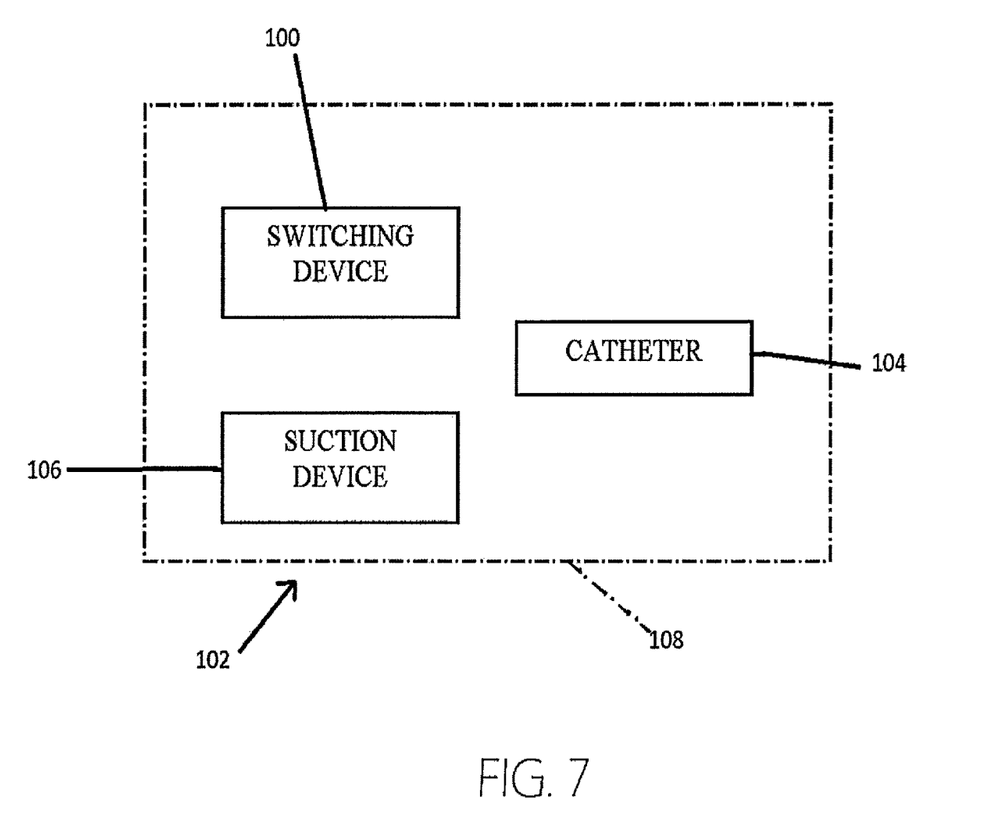
FIG. 7 is a block diagram of a kit containing a switching device pursuant to the present invention.

Moreover, it is advantageous to provide a kit 102 for bladder catheterization, comprising, as depicted in FIG. 7: a switching device 100 according to the invention; a three way bladder catheter 104, and a suction device 106 of liquids enclosed in a sterile or sterilizable pack 108.

The disclosed switching device 100 is obviously sterile or sterilizable.

What above described has been described only as a way of not limiting example, possible practice-applicative variants are intended to be in the protective scope of the invention as above described and claimed in the following.

The invention claimed is:

1. A fluid flow switching device for catheterization with a three way bladder catheter, comprising: a housing; first, second, third and fourth openings provided in the housing; first, second and third distal hydraulic conduits formed at the first, the second and the third openings, respectively; switching means designed for engaging with the housing such that in a first operative configuration the switching means permits communication between the first opening and the third opening, in a second operative configuration the switching means permits communication between the second opening and the fourth opening, in a third operative configuration the switching means permits communication between the first opening and the second opening, and in a fourth operative configuration the switching means permits communication between the second opening and the third opening; and a hydraulic bifurcation comprising: a proximal hydraulic branch extending from said fourth opening, and fourth and fifth distal hydraulic conduits extending from said proximal hydraulic branch and being in fluid communication with each other, wherein the first and second distal hydraulic conduits are parallel to the third and fourth distal hydraulic conduits.

2. Flow switching device according to claim 1, wherein the fifth distal hydraulic conduit has a respective longitudinal axis forming an angle between 135° and 160° with a longitudinal axis of the fourth distal hydraulic conduit.

3. Flow switching device according to claim 1, wherein the first and the second distal hydraulic conduits are aligned with each other.

4. Flow switching device according to claim 1, wherein the third and the fourth distal hydraulic conduits are aligned with each other.

5. Flow switching device according to claim 1, wherein the switching means is a single body.

6. Flow switching device according to claim 5, wherein the switching means comprises a first and a second hydraulic tube unitary and integral with a cylindrical surface of the switching means.

7. Flow switching device according to claim 6, wherein said first, second and third distal hydraulic conduits and the proximal hydraulic branch are unitary and integral with said housing; and wherein said hydraulic bifurcation is formed from a three way hydraulic fitting hydraulically connected to said proximal hydraulic branch.

8. Flow switching device according to claim 7, wherein a first way or branch of the three way hydraulic fitting is configured for coupling to said proximal hydraulic branch, and a second way or branch and a third way or branch define said fourth and fifth distal hydraulic conduits, respectively.

9. Flow switching device according to claim 1, wherein the first, second and third distal hydraulic conduits and the hydraulic bifurcation are external to the housing, wherein the switching means is at least introducible in the housing and comprises a greater hydraulic pipeline and a smaller hydraulic pipeline, and wherein the switching means including the greater hydraulic pipeline and the smaller hydraulic pipeline is configured to rotate in said housing at different angular positions relative to the housing; wherein in the first and the second operative configurations, the greater hydraulic pipeline connects only two not consecutive openings of the first, second, third and fourth openings to each other and the smaller hydraulic pipeline does not connect any of the first, second, third and fourth openings to each other; and wherein in the third and fourth operative configurations, the smaller hydraulic pipeline connects only two consecutive openings of the first, second, third and fourth openings to each other and the greater hydraulic pipeline does not connect any of the first, second, third and fourth openings to each other.

10. Flow switching device according to claim 9, wherein at least one of the greater hydraulic pipeline and the smaller hydraulic pipeline is rectilinear.

11. Flow switching device according to claim 10, wherein the greater hydraulic pipeline and the smaller hydraulic pipeline are parallel with respect to each other.

12. Flow switching device according to claim 9, wherein: the housing is cylindrical and is bound internally and laterally by a first cylindrical surface, the housing being accessible in parallel to the first cylindrical surface; the first, second, third and fourth openings arranged substantially along a circumference of the first cylindrical surface, one after the other and angularly spaced at a first angle between 80° and 100°; the switching means further comprising a second cylindrical surface with a hole, the switching means being introducible in said housing with said second cylindrical surface disposed in parallel to the first cylindrical surface and with such a close fit as to allow the switching means to be held in said housing and to close at least two openings of the first, second, third and fourth openings at different angular positions of the switching means; wherein the greater hydraulic pipeline is internal to the second cylindrical surface and configured to connect a first and a second through hole disposed in the second cylindrical surface and angularly spaced with respect to each other at a second angle between 170° and 190°; and the smaller hydraulic pipeline is internal to the second cylindrical surface, arranged laterally to the greater hydraulic pipeline and configured to connect a third and fourth through hole disposed in the second cylindrical surface laterally and substantially coplanarly to said first and second through holes, wherein said first, second, third and fourth openings and said first, second third and fourth through holes are configured and arranged so that with the second cylindrical surface introduced in the housing and with respective degrees of rotation of the second cylindrical surface with respect to the first cylindrical surface, the switching means is rotatable to said first, second, third and fourth operative configurations.

13. Flow switching device according to claim 12, wherein said first, second, third and fourth openings and, said first, second, third and fourth through holes have the same dimensions.

14. Flow switching device according to claim 12, wherein said switching means comprises a graspable element to rotate the switching means in the housing, the graspable element being disposed outside of the housing.

15. Flow switching device according to claim 12, wherein said first, second, third and fourth openings are arranged one after the other angularly and equidistant; said first and second through holes being disposed substantially diametrically with respect to each; and said third and fourth through holes being angularly spaced by a third angle substantially equal to 90°.

16. Flow switching device according to claim 15, wherein the first, second, third and fourth distal hydraulic conduits are substantially coplanar, rectilinear and inclined each at a predetermined angle between 20° and 45° with respect to a respective radial direction passing through a center of said circumference and through a center of one of the first, second, third and fourth openings.

17. Flow switching device according to claim 16, wherein the predetermined angle is between 35° and 45°.

18. Flow switching device according to claim 16, wherein the predetermined angle is substantially equal to 45°.

19. Kit for bladder catheterization, comprising: the flow switching device according to claim 1; a catheter; and a liquid suction device enclosed in a sterile or sterilizable pack.

* * * * *